United States Patent
Nolan et al.

(10) Patent No.: US 6,403,801 B1
(45) Date of Patent: Jun. 11, 2002

(54) USE OF A CATALYST SYSTEM COMPRISING NICKEL, PALLADIUM, OR PLATINUM AND IMIDAZOLINE-2-YLIDENE OF IMIDAZOLIDINE-2-YLIDENE IN SUZUKI COUPLING REACTIONS

(75) Inventors: Steven P. Nolan, New Orleans, LA (US); Jinkun Huang, Des Plaines, IL (US); Mark L. Trudell, Metairie; Chunming Zhang, New Orleans, both of LA (US)

(73) Assignee: University of New Orleans Research & Technology Foundation, New Orleans, LA (US)

( * ) Notice: Subject to any disclaimer, the term of this patent is extended or adjusted under 35 U.S.C. 154(b) by 0 days.

(21) Appl. No.: 09/507,959

(22) Filed: Feb. 22, 2000

Related U.S. Application Data

(60) Provisional application No. 60/121,056, filed on Feb. 22, 1999, and provisional application No. 60/154,260, filed on Sep. 16, 1999.

(51) Int. Cl.⁷ .................................................. C07F 9/80
(52) U.S. Cl. ....................................... 548/103; 548/110
(58) Field of Search ......................................... 548/103

(56) References Cited

U.S. PATENT DOCUMENTS

| | | | |
|---|---|---|---|
| 5,077,414 A | 12/1991 | Arduengo, III | 548/335 |
| 5,104,993 A | 4/1992 | Arguengo III | 548/317 |
| 5,703,269 A | 12/1997 | Hermann et al. | 560/19 |
| 5,728,839 A | 3/1998 | Hermann et al. | 548/103 |

OTHER PUBLICATIONS

Arduengo, III, et al., "Electronic Stabilization of Nucleophilic Carbenes", J. Am. Chem. Soc., 1992, vol. 114, No. 14, pp. 5530–5534.
Arduengo, III et al., "A Stable Diaminocarbene", J. Am. Chem. Soc., 1995, vol. 117, No. 44, pp. 11027–11028.
Hermann, et al., "Metal Complexes of N–Hetercyclic Carbenes—A New Structural Principle for Catalysts in Homogeneous Catalysis", Agnew Chem. Int. Ed. Engl., 1995, vol. 34, No. 21, pp. 2371–2374.
Hermann, et al., "N–Heterocyclic Carbenes[+]: Generation Under Mild Conditions and Formation of Group 8–10 Transition Metal Complexes Relevant to Catalysis", Chem. Eur. J. 1996, vol. 2, No. 7, pp. 772–780.
Hermann et al., "N–Heterocyclic Carbenes", Angew. Chem. Int. Ed. Engl., 1997, vol. 36, pp. 2162–2187.
Hermann et al., "Chelating N–heterocyclic Carbene Ligands in Palladium–Catalyzed Heck–Type Reactions", Journal of Organometallic Chem., 1998, vol. 557, pp. 93–96.
Huang, Jinkun et al., "Olefin Metathesis–Active Ruthenium Complexes Bearing a Nucleophilic Carbene Ligand", J. Am. Chem. Soc., 1999, vol. 121, No. 12, pp. 2674–2678.
Littke et al., "A Convenient and General Method for Pd–Catalyzed Suzuki Cross–Couplings of Aryl Chlorides and Arylboronic Acids", Angew. Chem. Int. Ed. 1998, vol. 37, No. 24, pp. 3387–3388.
McGuinness, et al., "Synthesis and Reaction Chemistry of Mixed Ligand Methylpalladium–Carbene Complexes", J. Organometallic Chem., 1998, vol. 565, pp. 165–178.
Old et al., "A Highly Active Catalysr for Palladium–Catalyzed Cross–Coupling Reactions: Room–Temperature Suzuki Couplings and Amination of Unactivated Aryl Chlorides", J. Am. Chem. Soc., 1998, vol. 120, pp. 9722–9723.
Zhang et al., "Palladium–Imidazol–2–Ylidene Complexes as Catalysts for Facile and Efficient Suzuki Cross–Coupling Reactions of Aryl Chlorides with Arylboronic Acids", J. Org. Chem., 1999, vol. 64, No. 11, pp. 3804–3805.
Alder, et al., "Stable Carbenes as Strong Bases", J. Chem. Soc., Chem. Commun, 1995, pp. 1267–1268.
Arduengo, III et al., "A Stable Crystalline Carbene", J. Am. Chem. Soc., 1991, vol. 113, No. 1, pp. 361–363.
Arduengo, III et al., "An Air Stable Carbene and Mixed Carbene Dimers", J. Am. Chem. Soc., 1997, vol. 119, No. 52, pp. 12742–12749.

(List continued on next page.)

Primary Examiner—Floyd D. Higel
Assistant Examiner—Ebenezer Sacket
(74) Attorney, Agent, or Firm—Sieberth & Patty, L.L.C.

(57) ABSTRACT

This invention provides a process for conducting Suzuki coupling reactions. The processes of the present invention make use of N-heterocyclic carbenes as ancillary ligands in Suzuki couplings of aryl halides and aryl pseudohalides. A Suzuki coupling can be carried out by mixing, in a liquid medium, at least one strong base; at least one aryl halide or aryl pseudohalide in which all substituents are other than boronic acid groups, wherein the aryl halide has, directly bonded to the aromatic ring(s), at least one halogen atom selected from the group consisting of a chlorine atom, a bromine atom, and an iodine atom; at least one arylboronic acid in which all substituents are other than chlorine atoms, bromine atoms, iodine atoms, or pseudohalide groups; at least one metal compound comprising at least one metal atom selected from nickel, palladium, and platinum, wherein the formal oxidation state of the metal is zero or two; and at least one N-heterocyclic carbene. One preferred type of N-heterocyclic carbene is an imidazoline-2-ylidene of the formula

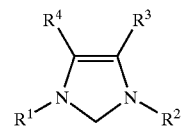

wherein $R^1$ and $R^2$ are each, independently, alkyl or aryl groups having at least 3 carbon atoms, $R^3$ and $R^4$ are each, independently, a hydrogen atom, a halogen atom, or a hydrocarbyl group.

69 Claims, No Drawings

OTHER PUBLICATIONS

Schönherr, et al., "1.3.4.5–Tetraphenyl–imidazoliumperchlorat", Liebigs Ann. Chem. Bd. 731, 1970, pp. 176–179 (not translated).

Chemical Abstracts, vol. 55, Col. 21100, Wanzlick et al., "New Contribution to Carbene Chemistry", Angew Chem. vol. 72, p. 494, 1960.

Brescia et al., "Stereoselective Phenylation of Allylic Alcohol Derivatives by Palladium–Catalyzed Cross–Coupling with Hypervalent Silicon Complexes", J. Org. Chem., vol. 63, No. 10, 1998, pp. 3156–3157.

Chuit et al., "Reactivity of Penta—and Hexacoordinate Silicon Compounds and Their Role as Reaction Intermediates", Chem. Rev., vol. 93, 1993, pp. 1371–1372 and 1440–1448.

Denmark et al., "Highly Stereospecific, Cross–Coupling Reactions of Alkenylsilacyclobutanes", J. Am. Chem. Soc., vol. 121, No. 24, 1999, pp. 5821–5822.

Denmark, et al., "Synthesis of Unsymmetrical Biaryls from Arylsilacyclobutanes", Organic Letters, vol. 1, No. 9, 1999, pp. 1495–1498.

Deiderich et al., editors, Metal–catalyzed Cross–coupling Reactions, Wiley–VCH Publishing, Chapter 10, author Hiyama "Organosilicon Compounds in Cross–coupling Reactions", 1999, pp. 421–453.

"Group Notation Revised in Periodic Table" Chemical & Engineering News, 1985, vol. 63, pp. 26–27.

Hiyama et al., "Palladium–catalyzed cross–coupling reaction of organometalloids through activation with fluoride ion", Pure and Applied Chem., vol. 66, No. 7, 1994, pp. 1471–1478.

Horn, Keith, "Regio—and Stereochemical Aspects of the Palladium–Catalyzed Reactions of Silanes", Chem. Rev., vol. 95, 1995, pp. 1317–1350.

Huang, et al., "General and Efficient Catalytic Animation of Aryl Chlorides Using a Palladium/Bulky Nucleophilic Carbene System", Org. Lett. 1999, vol. 1, No. 8, pp. 1307–1309.

Huang et al., "Efficient Cross–Coupling of Aryl Chlorides With Aryl Grignard Reagents (Kumada Reactiion) Mediated by a Palladium/Imidazolium Chloride System", J. Am. Chem. Soc., 1999, vol. 121, No. 42, pp. 9889–9890.

Mowery et al., "Improvements in Cross Coupling Reactions of Hypervalent Siloxane Derivatives", Organic Letters, vol. 1, No. 13, 1999, pp. 2137–2140.

Mowery et al., "Cross–Coupling Reactions of Hypervalent Siloxane Derivatives: An Alternative to Stille and Suzuki Couplings", J. Org. Chem., vol. 64, No. 5, 1999, pp. 1684–1688.

Mowery et al., "Synthesis of Unsymmetrical Biaryls by Palladium–Catalyzed Cross Coupling Reactions of Arenes with Tetrabutylammonium Triphenyldifluorosilicate, a Hypervalent Silicon Reagent", J. Org. Chem., vol. 64, No. 9, 1999, pp. 3266–3270.

Pilcher et al., "Utilization of Tetrabutylammonium Triphenyldifluorosilicate as a Fluoride Source for Silicon–Carbon Bond Cleavage", J. Org. Chem., vol. 61, No. 20, 1996, pp. 6901–6905.

Regitz, Manfred, "Nucleophilic Carbenes: An Incredible Renaissance", Angew. Chem. Int. Ed. Engl., 1996, vol. 35, No. 7, pp. 725–728.

Wanzlick et al., "Direct Synthesis of a Mercury Salt–Carbene Complex", Agnew Chem, Internat. Edit., 1968, vol. 7, No. 2, pp. 141–142 and 154.

Wolfe, et al., "A Highly Active Catalyst for the Room–Temperature Amination and Suzuki Coupling of Aryl Chlorides", Angew. Chem. Int. Ed., 1999, vol. 38, No. 16, pp. 2413–2416.

under Contract No. R01 DA11528/9631611. The Government has certain rights in this invention.

USE OF A CATALYST SYSTEM COMPRISING NICKEL, PALLADIUM, OR PLATINUM AND IMIDAZOLINE-2-YLIDENE OF IMIDAZOLIDINE-2-YLIDENE IN SUZUKI COUPLING REACTIONS

REFERENCE TO RELATED APPLICATIONS

This Application claims the priority date of U.S. Provisional Application No. 60/121,056, filed Feb. 22, 1999, and of U.S. Provisional Application No. 60/154,260 filed Sep. 16, 1999. U.S. Provisional Applications No. 60/121,056 and 60/154,260 incorporate by reference U.S. Provisional Application No. 60/099,722, filed Sep. 10, 1998.

Copending Application No. 09/511,420, filed Feb. 22, 2000, by us; copending application Ser. No. 09/511,122, filed Feb. 22, 2000, by us; copending application Ser. No. 09/507,958, filed Feb. 22, 2000, by us; and copending application Ser. No 09/511,654, filed Feb. 22, 2000, by us; may possibly be considered related to the present application.

This invention was made with Government support by the National Institute on Drug Abuse/National Science Foundation under Contract No. R01 DA11528/9631611. The Government has certain rights in this invention.

TECHNICAL FIELD

This invention relates to Suzuki coupling reactions, which can be used for chemical synthesis in the polymer and the fine chemical industry.

BACKGROUND

The palladium catalyzed Suzuki cross-coupling reaction of aryl bromides, aryl iodides, and aryl pseudohalides (e.g., triflates) is a general method employed for the formation of C—C bonds. Prior art methods generally cannot employ aryl chlorides as feedstock for these chemical transformations, and require the use of more expensive aryl bromides and aryl iodides. The use of aryl chlorides as chemical feedstock in coupling chemistry has proven difficult but would economically benefit a number of industrial processes. The few prior art methods that can employ aryl chlorides use expensive, air-sensitive phosphine ligands. See in this connection Old et al., *J. Am. Chem. Soc.*, 1998, 120, 9722–9723, and Littke and Fu, *Angew. Chem. Int. Ed. Engl.*, 1998, 37, 3387–3388, which describe phosphine-modified, palladium-mediated Suzuki coupling reactions which employ aryl chlorides as substrates. The use of a bulky phosphine (e.g., tri(tert-butyl) phosphine) or phosphine-containing moiety (e.g., di(cyclohexyl)phosphino) in ancillary ligation was shown to be fundamental in triggering the observed catalytic behavior. In addition, these phosphine ligands are often difficult to remove from the process product.

Nucleophilic N-heterocyclic carbenes, the imidazoline-2-ylidenes (sometimes commonly called imidazol-2-ylidenes) or so-called "phosphine mimics", have attracted considerable attention as possible alternatives for the widely used phosphine ligands in homogeneous catalysis. A primary advantage of these ligands is that an excess of the ligand is not required. It appears that these ligands do not dissociate from the metal center, thus preventing aggregation of the catalyst to yield the bulk metal.

In fact, Herrmann et al., in *J. Organometallic Chem.*, 1998, 557, 93–96, have reported Suzuki coupling activity using carbene ancillary ligands with aryl bromides and an activated aryl chloride as substrates. While these carbene ligands are thermally stable, the reported reaction times were long, and the yield from the aryl chloride was relatively low.

THE INVENTION

This invention provides a process for conducting Suzuki coupling reactions. The catalyst system used in the present invention exhibits the fastest reaction rate for Suzuki coupling observed to date, 3 times faster than the best reported rate for a phosphine-based catalyst system. The catalyst system of the present invention permits the use of aryl chlorides as substrates in Suzuki coupling reactions while eliminating the need for phosphine ligands. Furthermore, both electron-donating and electron-withdrawing substituents on the aryl halide or pseudohalide, the arylboronic acid, or both, in the Suzuki coupling reaction are well tolerated by the catalyst system of the present invention, and provide the corresponding Suzuki coupling products in excellent yields.

An embodiment of this invention provides a process which comprises mixing, in a liquid medium, i) at least one strong base; ii) at least one aryl halide or aryl pseudohalide in which all substituents are other than boronic acid groups, wherein the aryl halide has, directly bonded to the aromatic ring(s), at least one halogen atom selected from the group consisting of a chlorine atom, a bromine atom, and an iodine atom; iii) at least one arylboronic acid in which all substituents are other than chlorine atoms, bromine atoms, iodine atoms, or pseudohalide groups; iv) at least one metal compound comprising at least one metal atom selected from nickel, palladium, and platinum, wherein the formal oxidation state of the metal is zero or two; and v) at least one N-heterocyclic carbene. The N-heterocyclic carbene is selected from the group consisting of an imidazoline-2-ylidene wherein the 1 and 3 positions are each, independently, substituted by a secondary or tertiary group which has at least three atoms, or a protonated salt thereof; an imidazolidine-2-ylidene wherein the 1 and 3 positions are each, independently, substituted by a secondary or tertiary group which has at least three atoms, or a protonated salt thereof; a bis(imidazoline-2-ylidene) wherein a bridging moiety is bound to one nitrogen atom of each ring, and wherein the remaining two nitrogen atoms are each, independently, substituted by a secondary or tertiary group which has at least three atoms, or a protonated salt thereof; a bis(imidazolidine-2-ylidene) wherein a bridging moiety is bound to one nitrogen atom of each ring, and wherein the remaining two nitrogen atoms are each, independently, substituted by a secondary or tertiary group which has at least three atoms, or a protonated salt thereof; and mixtures of two or more of the foregoing.

Further embodiments and features of this invention will be apparent from the ensuing description and appended claims.

The liquid medium for the processes of this invention can include any of a wide range of solvents, and mixtures of solvents are also usable. The exclusion of water is not necessary, but is preferred. Types of solvents that can be used include hydrocarbons, ethers, amides, ketones, and alcohols. Polar solvents are preferred; ethers are a more preferred Solvent type. Ethers that may be used include, for example, diethyl ether, di-n-propyl ether, diisopropyl ether, tert-butyl ethyl ether, diheptyl ether, 1,3-dioxolane, 1,4-dioxane, tetrahydrofuran, methyltetrahydrofuran, glyme (the dimethyl ether of ethylene glycol), diglyme (the dimethyl ether of diethylene glycol), and the like. Cyclic ethers and polyethers are preferred; a highly preferred ether is 1,4-dioxane.

A large variety of strong bases are suitable for use in the processes of this invention. Generally, these are inorganic bases. Alkali metal salts are a preferred group of inorganic bases. Examples of suitable alkali metal salts include, but are not limited to, sodium acetate, sodium bicarbonate, sodium tert-butoxide, sodium oxide, sodium tetrafluoroborate, potassium acetate, potassium carbonate, potassium tert-butoxide, potassium nitrite, potassium phosphate, potassium sulfite, potassium hexafluorophosphate, cesium acetate, cesium bicarbonate, cesium carbonate, cesium fluoride, cesium nitrate, and cesium sulfate. Alkali metal salts of carboxylic acid anions (e.g., acetate, trifluoroacetate, citrate, formate, oxalate, propionate, tartrate, etc.) are also suitable for use as the inorganic base in this invention. More preferred are salts of potassium and cesium; most preferred are cesium salts. The most highly preferred inorganic base is cesium carbonate. Choice(s) of inorganic base will vary with the particular system of aryl halide or pseudohalide and arylboronic acid involved. Amine bases are generally not preferred because, to date, they appear to poison the catalyst system of the invention.

Directly bonded to the aromatic ring(s) of the aryl halide or pseudohalide (i.e., aryl halide or aryl pseudohalide) is at least one halogen atom selected from a chlorine atom, a bromine atom, and an iodine atom, or at least one pseudohalide group. The term "pseudohalide group" includes such groups as p-toluenesulfonate(tosylate), and trifluoromethanesulfonate(triflate). The aryl halide or pseudohalide can have two or more such halogen atoms with an atomic number greater than nine and/or pseudohalide groups, including combinations of halogen atoms and pseudohalide groups. However, when two or more such groups are present, the halogen atoms with an atomic number greater than nine and/or pseudohalide groups should all be different from each other. For example, when two such substituents are present, they may be a chlorine atom and a bromine atom, or an iodine atom and a tosylate group, or etc. It is preferred that there is only one chlorine atom, bromine atom, iodine atom, or pseudohalide group directly bound to the aryl ring of the aryl halide or pseudohalide. Aryl chlorides are more preferred as the aryl halide reactants. To prevent self-reaction, it is preferred that boronic acid groups are not present on the aryl halide or pseudohalide.

The aryl moiety for the aryl halide or pseudohalide can be homocyclic or heterocyclic. Examples of suitable homocyclic aryl moieties include, but are not limited to, benzene, naphthalene, anthracene, phenanthrene, pyrene, biphenyl, acenaphthalene, fluorene, and indene. Heterocyclic aryl moieties that can be used include, for example, furan, thiophene, oxathiolane, thianthrene, isobenzofuran, phenoxathiin, and the like. Nitrogen-containing heterocycles, such as pyridine, indole, and isoxazole may have an effect on the catalyst system similar to that of amine bases, as described above, and thus are not preferred. Benzene is a preferred aryl moiety for the aryl halide or pseudohalide.

For the aryl halide or pseudohalide, substituents other than a chlorine atom, a bromine atom, an iodine atom, and/or a pseudohalide group that may be present on the aromatic ring(s) include, but are not limited to, hydrogen atoms, fluorine atoms, nitro groups, hydrocarbyl groups, alkoxy groups, perfluorohydrocarbyl groups, silyl groups, ether groups, ketone groups, and ester groups. When hydrocarbyl groups are present, they are preferably $C_1$ to $C_{18}$ alkyl groups or $C_6$ to $C_{20}$ aryl or aralkyl groups. Examples of suitable hydrocarbyl groups are methyl, ethyl, isopropyl, tert-butyl, cyclopentyl, methylcyclohexyl, decyl, phenyl, tolyl, xylyl, benzyl, naphthyl, and tetrahydronaphthyl. Alkoxy group substituents preferably have $C_1$ to $C_6$ alkyl moieties. Some examples of alkoxy groups are methoxy, ethoxy, isopropoxy, methylcyclopentoxy, and cyclohexoxy. Perfluorohydrocarbyl groups include alkyl and aryl perfluorocarbons; suitable perfluorohydrocarbyl groups are, for example, trifluoromethyl, pentafluoroethyl, pentafluorophenyl, and heptafluoronaphthyl. Substituent silyl groups preferably have $C_1$ to $C_{18}$ alkyl groups or $C_6$ to $C_{20}$ aryl or aralkyl groups, and examples include trimethylsilyl, triisopropylsilyl, tert-butyl(dimethyl)silyl, tridecylsilyl, and triphenylsilyl. The substituents preferred for the aryl halide or pseudohalide will depend on the product that is desired.

It is preferred that the arylboronic acid contains only one boronic acid group directly bonded to the aromatic ring(s), which may prevent mixtures of products from forming. It is recognized that more than one boronic acid group may be present when a mixture of products is desired. To prevent self-reaction, it is also preferred that chlorine atoms, bromine atoms, iodine atoms, and/or pseudohalide groups are not present on the aromatic ring(s) of the arylboronic acid. In other words, the arylboronic acid is preferably devoid of halogen atoms with an atomic number greater than nine, and is also preferably devoid of pseudohalide groups. However, one or more fluorine atoms can be present on the aromatic ring(s).

The aryl moiety of the arylboronic acid can be homocyclic or heterocyclic, as described for the aryl halide or pseudohalide. For the arylboronic acid, the preferred aryl moieties are benzene and naphthalene. Substituents on the aryl ring, again as described for the aryl halide or pseudohalide, can be hydrogen atoms, fluorine atoms, nitro groups, hydrocarbyl groups, alkoxy groups, perfluorohydrocarbyl groups, silyl groups, ether groups, ketone groups, and ester groups. Preferred substituents for the arylboronic acid depend on the desired product.

The metal compound comprises at least one metal atom selected from nickel, palladium, and platinum having a formal oxidation state of zero or two, and is sometimes referred to hereinafter as the metal compound. Inorganic salts of nickel, palladium, or platinum that can be used include the bromides, chlorides, fluorides, iodides, cyanides, nitrates, sulfides, sulfites, and sulfates. Organic nickel, palladium, or platinum compounds that may be used include complexes and salts such as the carboxylates, e.g., the acetates or propionates, etc. Suitable nickel compounds include bis(1,5-cyclooctadiene)nickel, nickel acetate, nickel oxalate, nickel phosphate, nickel stearate, nickel acetylacetonate, nickel tetrafluoroborate, nickel thiocyanate, nickel carbonate, and nickel sulfamate. Examples of palladium compounds include $Pd(OAc)_2$, palladium(II)chloride, $Pd(CH_3CN)_4(BF_4)_2$, tris(dibenzylideneacetone)dipalladium (0) [which is also referred to herein as dipalladium tris (dibenzylideneacetone)], and palladium trifluoroacetate. Platinum compounds that can be used include platinum acetylacetonate and platinum chloride. Nickel and palladium compounds are preferred; more preferred are compounds of palladium. Palladium compounds such as palladium acetate and tris(dibenzylideneacetone)dipalladium(0) are most preferred.

Preferred types of N-heterocyclic carbenes are imidazoline-2-ylidenes of the formula

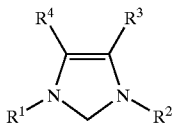

or protonated salts thereof, wherein $R^1$ and $R^2$ are each, independently, alkyl or aryl groups having at least 3 carbon atoms, $R^3$ and $R^4$ are each, independently, a hydrogen atom, a halogen atom, or a hydrocarbyl group; imidazolidine-2-ylidenes of the formula

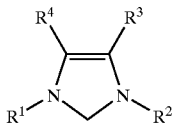

or protonated salts thereof, wherein $R^1$, $R^2$, $R^3$, and $R^4$ are as defined for the imidazoline-2-ylidenes; bis(imidazoline-2-ylidene)s of the formula

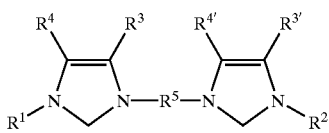

or protonated salts thereof, wherein $R^1$, $R^2$, $R^3$, and $R^4$ are as defined for the imidazoline-2-ylidenes, wherein $R^{3'}$ and $R^{4'}$ are as defined for $R^3$ and $R^4$ for the imidazoline-2-ylidenes, and wherein $R^5$ is a bridging group that links the two imidazoline rings; bis(imidazolidine-2-ylidene)s of the formula

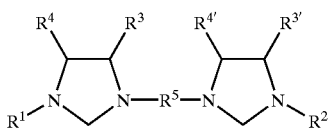

or protonated salts thereof, wherein $R^1$, $R^2$, $R^3$, and $R^4$ are as defined for the imidazoline-2-ylidenes, wherein $R^{3'}$ and $R^{4'}$ are as defined for $R^3$ and $R^4$ for the imidazoline-2-ylidenes, and wherein $R^5$ is a bridging group that links the two imidazolidine rings.

$R^1$ and $R^2$ are preferably sterically bulky groups. Suitable groups include, but are not limited to, isopropyl, sec-butyl, tert-butyl, 2,2-dimethylpropyl(neopentyl), cyclohexyl, norbornyl, adamantyl, tolyl, 3,5-dimethylphenyl, 2,4,6-trimethylphenyl, 2,6-diisopropylphenyl, and triphenylmethyl. Preferred groups are tert-butyl, 2,4,6-trimethylphenyl, 2,6-diisopropylphenyl, and triphenylmethyl. Most preferred for both $R^1$ and $R^2$ are the 2,4,6-trimethylphenyl and 2,6-diisopropylphenyl groups.

Examples of suitable $R^3$, $R^4$, $R^{3'}$, and $R^{4'}$ groups include chlorine atoms, bromine atoms, hydrogen atoms, hydrocarbyl groups, and the like. When hydrocarbyl groups are present, they are preferably $C_1$ to $C_{18}$ alkyl groups or $C_6$ to $C_{20}$ aryl or aralkyl groups. Examples of suitable hydrocarbyl groups are methyl, ethyl, isopropyl, tert-butyl, cyclopentyl, methylcyclohexyl, decyl, phenyl, tolyl, xylyl, benzyl, naphthyl, and tetrahydronaphthyl. Chlorine atoms and hydrogen atoms are preferred groups. Most preferred for all substituents $R^3$, $R^4$, $R^{3'}$, and $R^{4'}$ are hydrogen atoms.

$R^5$ in both the formula for the bis(imidazoline-2-ylidene)s and the bis(imidazolidine-2-ylidene)s of this invention can be selected from a large variety of moieties, including alkylene groups, arylene groups, and silylene groups. Atoms that can form the bridge include, but are not limited to, carbon, nitrogen, oxygen, silicon, and sulfur. Examples of suitable bridging moieties include methylene ($-CH_2-$), substituted methylene, ethylene ($-CH_2CH_2-$), substituted ethylene, silylene ($>SiR_2$), benzo ($C_6H_4<$), substituted benzo, biphenylene, substituted biphenylene, binaphthylene, and substituted binaphthylene. Heterocyclic aromatic moieties such as, for example, pyridine, pyrimidine, pyrazine, pyridazine, furan, thiophene, oxathiolane, thianthrene, isobenzofuran, phenoxathiin, isothiazole, phenoxazine, and the like, can also form the bridge. Preferred $R^5$ moieties include biphenylene, binaphthylene, and substituted benzo, with substituted benzo being more preferred. Highly preferred is benzo substituted with methyl groups. The bridge preferably has at least four atoms, and more preferably has from four to eight atoms. While better results have been observed with longer bridges, it is possible that judicious choices for $R^1$, $R^2$, $R^3$, $R^4$, $R^{3'}$, and $R^{4'}$ may improve results for short bridges.

Without being bound by theory, it appears from thermochemical studies that the electron-donating ability of many of the imidazoline-2-ylidene carbene ligands is better than that of tri(cyclohexyl)phosphine and the steric demand of these carbene ligands is greater than that of tri(cyclohexyl)phosphine. This suggests that the N-heterocyclic carbene should possess steric bulk sufficient to stabilize both the free carbene and to stabilize reaction intermediates. However, imidazoline-2-ylidene carbenes and imidazolidine-2-ylidene carbenes are considerably less stable to air and moisture than their corresponding protonated imidazolinium and imidazolidinium salts. Thus, a highly preferred embodiment of this invention involves generation of the imidazoline-2-ylidene in situ from the corresponding imidazolinium salt (similarly so for the imidazolidine-2-ylidene and the corresponding imidazolidinium salt); this removes the need to handle the N-heterocyclic carbene ligands in an inert atmosphere. Protonated salts of the imidazoline-2-ylidene carbenes and imidazolidine-2-ylidene carbenes are monoprotonated, while the protonated salts of the bis(imidazoline-2-ylidene)s and the bis(imidazolidine-2-ylidene)s are diprotonated. Suitable counterions for the protonated salts are virtually limitless, but halides are preferred counterions. The most preferred counterions are chloride and bromide. The imidazolinium salts are straightforward to synthesize and are air-stable. While the absence of oxygen is not necessary when using a protonated salt of an imidazoline-2-ylidene carbene or an imidazolidine-2-ylidene carbene, it is preferred. When using a neutral carbene, the absence of oxygen is necessary. In any instance where oxygen is excluded, the presence of an inert gas such as nitrogen, helium, or argon is preferred.

The aryl halide or pseudohalide and the arylboronic acid may be employed in an ideal molar ratio of about 1:1 when using an aryl halide or pseudohalide that has only one halogen atom (other than a fluorine atom) or pseudohalide group; or either reagent may be used in excess. It is preferred to use the arylboronic acid in an excess such that the molar ratio of aryl halide or pseudohalide to arylboronic acid is in the range of from about 1:1 to about 1:3 when using an aryl halide or pseudohalide that has only one halogen atom (other than a fluorine atom) or pseudohalide group. When the aryl halide or pseudohalide has more than one halogen atom (other than fluorine) and/or pseudohalide group, reactions may be carried out in sequence. An arylboronic acid will react first at the site of the more reactive substituent, e.g., at iodine before bromine. Reaction at only the site of the more reactive substituent(s) can be performed. In reactions carried out in sequence where the arylboronic acids are different, each should be added separately. It is preferred to allow one reaction to finish before the addition of the next arylboronic acid. When different arylboronic acids are used, it is preferred to use close to the ideal molar ratio of aryl halide or pseudohalide to arylboronic acid to minimize undesirable side products.

A suitable molar ratio of aryl halide or pseudohalide to strong base is in the range of from about 1:1 to about 1:5. A more preferred molar ratio of aryl halide or pseudohalide to strong base is in the range of from about 1:1 to about 1:3.

Normally, the molar ratio of metal atoms of the metal compound to aryl halide or pseudohalide molecules is in the range of from about 0.01:1 to about 0.05:1; a preferred molar ratio of metal atoms of metal compound to aryl halide or pseudohalide molecules is in the range of from about 0.02:1 to about 0.04:1. For the metal compound and the carbene ligands, the molar ratio of metal atoms of the metal compound to carbene molecules is in the range of from about 1:0.5 to about 1:5, and more preferably in the range of from about 1:1 to about 1:3.

The order of addition of the various components to a reaction vessel is not of particular importance. Premixing of the components of the catalyst system is not necessary; however, it is preferred that the catalyst system is premixed. To premix the components of the catalyst system, the metal compound, the N-heterocyclic carbene (salt or neutral compound), and the strong base are mixed together after being added in no particular order to a reaction vessel. The mixing time (activation period) for these components on the laboratory scale may be very short, e.g., five minutes or less, but a preferred mixing time is in the range of from about fifteen minutes to about sixty minutes.

If a premixed catalyst system is used, the aryl halide or pseudohalide and the arylboronic acid may be added to the same reaction vessel, or the premixed catalyst system can be transferred to a different vessel in which the reaction is to take place. Use of the same vessel for premixing the catalyst system and conducting the reaction is preferred.

When the components of the catalyst system are not premixed, the strong base, aryl halide or pseudohalide, the arylboronic acid, the metal compound, the liquid medium, and the N-heterocyclic carbene (salt or neutral compound) are added in any order to the reaction vessel.

Once all of the components are present in the same reaction vessel, the mixture may be heated, provided that the temperature does not exceed the thermal decomposition temperature of the catalyst system or the products of the reaction. Preferred temperatures are in the range of from about 20° C. to about 150° C.; more preferred temperatures are in the range of from about 20° C. to about 110° C. When the aryl halide or pseudohalide is an aryl chloride, an aryl triflate, or an aryl tosylate, heat is usually necessary to drive the reaction. Preferred temperatures when the aryl halide or pseudohalide is an aryl chloride, an aryl triflate, or an aryl tosylate are in the range of from about 40° C. to about 150° C. When the aryl halide or pseudohalide is an aryl bromide or an aryl iodide, the reaction(s) proceeds easily at room temperature, although heat may speed the reaction. For aryl bromides and aryl iodides, preferred temperatures are in the range of from about 20° C. to about 70° C.

While not necessary when using protonated salts of N-heterocyclic carbenes, the absence of oxygen and water is preferred when conducting the processes of this invention. Conversely, the exclusion of oxygen and water is generally necessary when neutral carbenes are used. The presence of an inert gas such as argon or nitrogen is preferred when oxygen and/or water are excluded. The reaction mixture is normally agitated. A preferred contact time for the components of the reaction is in the range of from about one hour to about forty-eight hours. More preferably, the contact time is from about one hour to about twenty-four hours.

The following examples are presented for purposes of illustration, and are not intended to impose limitations on the scope of this invention.

EXAMPLES

General Procedures

Reagents. All aryl chlorides (Aldrich Chemical Company), arylboronic acids (Aldrich), triethylamine (J.T. Baker Incorporated), $Na_2CO_3$ (EM Science), $K(CH_3CO_2)$ (EM Science), $K_2CO_3$ (EM Science), CsF (Aldrich), $Cs_2CO_3$ (Aldrich), and $Pd_2(dibenzylideneacetone)_3$ were used as received. 1,4-Dioxane was distilled from Na/benzophenone ketyl. Flash chromatography was performed on silica gel 60 (230–400 mesh; Natland International Corporation).

1,3-bis(2,4,6-trimethylphenyl)imidazoline-2-ylidene and 1,3-Bis(2,4,6-tri-methylphenyl)imidazolinium chloride were prepared according to reported procedures in U.S. Pat. No. 5,077,414, and/or Arduengo, A. J. III., Dias, H. V. R.; Harlow, R. L. and Kline, M. *J. Am. Chem. Soc.*, 1992, 114, 5530–5534.

Analyses. All reactions were monitored by thin layer chromatography (TLC). $^1H$ and $^{13}C$ nuclear magnetic resonance (NMR) spectra were recorded on a 300 MHz NMR spectrometer (Varian, Incorporated) or 400 MHz NMR spectrometer (Varian) at ambient temperature in $CDCl_3$ (Cambridge Isotope Laboratories, Incorporated). All of the products, which are known compounds, had $^1H$ NMR spectra identical with literature data.

Conditions. All reactions were carried out under an atmosphere of argon in oven-dried glassware with magnetic stirring, unless otherwise indicated.

Example 1

For each run, a Schlenk tube was charged with $Pd_2$ $(dibenzylideneacetone)_3$ (14 mg, 0.015 mmol), 1,3-bis(2,4,6-trimethylphenyl)imidazolinium chloride (10 mg, 0.03 mmol), base (2.00 equivalents), and a magnetic stirring bar. After a 30 minute catalyst activation period, 1,4-dioxane (3 mL), 4-chlorotoluene (1.0 mmol), and phenylboronic acid (1.5 mmol) were added in turn to the Schlenk tube. The Schlenk tube was placed in a 80° C. oil bath and the mixture was stirred for a number of hours. The mixture was then allowed to cool to room temperature. The reaction mixture was purified either directly by flash chromatography, or filtered through a pad of Celite® (desiccant), concentrated, and then purified by flash chromatography.

The base used in each run is listed in Table 1. All of the yields reported in Table 1 are of the heterocoupling product, and are the average of two runs. Reaction times reported in Table 1 do not include the 30 minute catalyst activation period.

TABLE 1

| Run | Base | Reaction time | Isolated yield |
|---|---|---|---|
| a | Et$_3$N | 24 hr. | <5%[a,b] |
| b | Na$_2$CO$_3$ | 43 hr. | 6%[a] |
| c | KOAc | 43 hr. | 42%[a] |
| d | K$_2$CO$_3$ | 24 hr. | 53% |
| e | CsF | 2 hr. | 65% |
| f | Cs$_2$CO$_3$ | 1.5 hr. | 96% |

[a]4-Chlorotoluene was not completely consumed within the indicated reaction time (by TLC).
[b]Precipitation of Pd black was observed.

Example 2

Reagents, analyses, and procedures were as described in Example 1, except as follows. The base for all runs was Cs$_2$CO$_3$ (652 mg, 2.00 mmol). Several different aryl chlorides (1.0 mmol each) and arylboronic acids (1.5 mmol each) were used. The mixture in the Schlenk tube was stirred for 1.5 hours in the oil bath. The aryl chlorides and arylboronic acids used in each run are listed in Table 2. All of the yields reported in Table 2 are of the heterocoupling product, and are the average of two runs.

TABLE 2

| Run | Aryl chloride | Arylboronic acid | Isolated yield |
|---|---|---|---|
| a | 4-Chlorotoluene | Phenylboronic acid | 96% |
| b | 4-Chlorotoluene | Phenylboronic acid | 97%[a] |
| c | 4-Chlorotoluene | 4-Methoxyphenylboronic acid | 99% |
| d | 4-Chlorotoluene | 2-Methoxyphenylboronic acid | 88% |
| e | 4-Chlorotoluene | 3-Methoxyphenylboronic acid | 91% |
| f | 4-Chlorobenzene | 4-Methoxyphenylboronic acid | 99% |
| g | 1,4-Dimethyl-2-chlorobenzene | Phenylboronic acid | 89% |
| h | 1-Methoxy-4-chlorobenzene | Phenylboronic acid | 93% |
| i | Methyl-4-chlorobenzoate | Phenylboronic acid | 99% |

[a]6.0 mol % of 1,3-bis(2,4,6-trimethylphenyl)imidazolinium chloride was used.

Example 3

Reagents, analyses, and procedures were as described in Example 1, except as follows. The base (2.00 mmol) was either Cs$_2$CO$_3$ or K$_2$CO$_3$; the metal compound was either Pd(CH$_3$CO$_2$)$_2$ (5.8 mg, 0.025 mmol) or Pd$_2$(dibenzylideneacetone)$_3$ (18.8 mg, 0.01 mmol); and the N-heterocyclic carbene was 1,3-bis(2,6-diisopropylphenyl) imidazolinium chloride (106 mg, 0.03 mmol). The aryl halide or pseudohalide in all runs was 4-methylphenyl p-toluenesulfonate (1.0 mmol). Several different arylboronic acids (1.5 mmol each) were used. The mixture in the Schlenk tube was stirred for 1.5 hours in the oil bath. The arylboronic acid, metal compound, and base used in each run are listed in Table 3. All of the yields reported in Table 3 are of the heterocoupling product, and are the average of two runs.

TABLE 3

| Run | Base | Metal compound | Arylboronic acid | Isolated yield |
|---|---|---|---|---|
| a | Cs$_2$CO$_3$ | Pd(CH$_3$CO$_2$)$_2$ | Phenylboronic acid | 94% |
| b | K$_2$CO$_3$ | Pd(CH$_3$CO$_2$)$_2$ | 4-Methylphenylboronic acid | 4.6% |
| c | Cs$_2$CO$_3$ | Pd$_2$(dibenzylideneacetone)$_3$ | Phenylboronic acid | 94% |
| d | K$_2$CO$_3$ | Pd$_2$(dibenzylideneacetone)$_3$ | 4-Methylphenylboronic acid | 98% |

Example 4

Reagents, analyses, and procedures were as described in Example 1, except as follows. The base (2.00 mmol) was either Cs$_2$CO$_3$ or K$_2$CO$_3$; the metal compound was either Pd(CH$_3$CO$_2$)$_2$ (5.6 mg, 0.025 mmol) or Pd$_2$(dibenzylideneacetone)$_3$ (18.8 mg, 0.01 mmol); and the N-heterocyclic carbene was 1,3-bis(2,6-diisopropylphenyl) imidazolinium chloride (106 mg, 0.03 mmol). Several different aryl triflates (1.0 mmol each) and arylboronic acids (1.5 mmol each) were used. The mixture in the Schlenk tube was stirred for 1.5 hours in the oil bath. The aryl triflate, arylboronic acid, metal compound, and base used in each run are listed in Table 4. All of the yields reported in Table 4 are of the heterocoupling product, and are the average of two runs.

TABLE 4

| Run | Base | Metal compound | Aryl Triflate | Arylboronic acid | Isolated yield |
|---|---|---|---|---|---|
| a | Cs$_2$CO$_3$ | Pd(CH$_3$CO$_2$)$_2$ | 4-methoxyphenyl triflate | Phenylboronic acid | 86% |
| b | K$_2$CO$_3$ | Pd(CH$_3$CO$_2$)$_2$ | 4-methoxyphenyl triflate | 4-Methylphenylboronic acid | 75% |
| c | Cs$_2$CO$_3$ | Pd(CH$_3$CO$_2$)$_2$ | 4-methoxyphenyl triflate | 4-Methoxyphenylboronic acid | 81% |
| d | K$_2$CO$_3$ | Pd(CH$_3$CO$_2$)$_2$ | Phenyl triflate | Phenylboronic acid | 52% |
| e | K$_2$CO$_3$ | Pd(CH$_3$CO$_2$)$_2$ | Phenyl triflate | 4-Methylphenylboronic acid | 99+% |
| f | Cs$_2$CO$_3$ | Pd(CH$_3$CO$_2$)$_2$ | Phenyl triflate | 4-Methoxyphenylboronic acid | 85% |
| g | Cs$_2$CO$_3$ | Pd(CH$_3$CO$_2$)$_2$ | 4-CH$_3$CO$_2$-phenyl triflate | Phenylboronic acid | 76% |
| h | K$_2$CO$_3$ | Pd(CH$_3$CO$_2$)$_2$ | 4-CH$_3$CO$_2$-phenyl triflate | 4-Methylphenylboronic acid | 93% |
| i | Cs$_2$CO$_3$ | Pd(CH$_3$CO$_2$)$_2$ | 4-CH$_3$CO$_2$-phenyl triflate | 4-Methoxyphenylboronic acid | 77% |
| j | Cs$_2$CO$_3$ | Pd$_2$(dibenzylideneacetone)$_3$ | 4-methoxyphenyl triflate | Phenylboronic acid | 97% |
| k | Cs$_2$CO$_3$ | Pd$_2$(dibenzylideneacetone)$_3$ | 4-methoxyphenyl triflate | 4-Methylphenylboronic acid | 98% |
| l | K$_2$CO$_3$ | Pd$_2$(dibenzylideneacetone)$_3$ | Phenyl triflate | Phenylboronic acid | 98% |

TABLE 4-continued

| Run | Base | Metal compound | Aryl Triflate | Arylboronic acid | Isolated yield |
|---|---|---|---|---|---|
| m | $Cs_2CO_3$ | $Pd_2$(dibenzylideneacetone)$_3$ | Phenyl triflate | 4-Methylphenylboronic acid | 99% |
| n | $K_2CO_3$ | $Pd_2$(dibenzylideneacetone)$_3$ | 4-$CH_3CO_2$-phenyl triflate | Phenylboronic acid | 55% |
| o | $Cs_2CO_3$ | $Pd_2$(dibenzylideneacetone)$_3$ | 4-$CH_3CO_2$-phenyl triflate | 4-Methylphenylboronic acid | 97% |

Example 5

Reagents, analyses, and procedures were as described in Example 1, except as follows. The base was $Cs_2CO_3$ (652 mg, 2.00 mmol); the metal compound was bis(1,5-cyclooctadiene)nickel (8.3 mg, 0.03 mmol, or 16.7 mg, 0.06 mmol); and the N-heterocyclic carbene was 1,3-bis(2,6-diisopropylphenyl)imidazolinium chloride (106 mg, 0.03 mmol). Several different aryl chlorides (1.0 mmol each) and aryl triflates (1.0 mmol each) were used. The arylboronic acid for all runs was phenylboronic acid (1.5 mmol). The mixture in the Schlenk tube was stirred for 48 hours in the oil bath. The aryl chloride or aryl triflate and the amount of bis(1,5-cyclooctadiene)nickel used in each run are listed in Table 5. All of the yields reported in Table 5 are of the heterocoupling product, and are the average of two runs.

TABLE 5

| Run | Amount of bis(1,5-cyclooctadiene)nickel | Aryl chloride or aryl triflate | Isolated yield |
|---|---|---|---|
| a | 0.03 mmol | 4-Chlorotoluene | 10% |
| b | 0.03 mmol | 1-Methoxy-4-chlorobenzene | 5% |
| c | 0.03 mmol | Methyl-4-chlorobenzoate | 10% |
| d | 0.06 mmol | 4-Chlorotoluene | 8% |
| e | 0.06 mmol | Methyl-4-chlorobenzoate | 48% |
| f | 0.06 mmol | 4-methylphenyl triflate | NR%[a] |
| g | 0.06 mmol | 4-methylphenyl triflate | <5% |
| h | 0.06 mmol | 4-methoxyphenyl triflate | 12% |
| i | 0.06 mmol | 4-$CH_3CO_2$-phenyl triflate | 5% |

[a]NR = no reaction; no carbene was used in this run.

Example 6

Six bis(imidazolinium) salts (see Table 6) were prepared by heating the dibromide or dichloride of the molecule intended to be the bridging moiety with two equivalents of an 1-aryl-imidazol in xylene. As an example, a mixture of dibromomethane (1.0 mmol) and N-(3,5-dimethylphenyl) imidazoline (2.0 mmol) was heated in xylene (5 mL) at 140° C. for 2 days. This afforded the salt shown in Run B of Table 6 in 70% yield. Alternatively, a mixture of 1,3-di(α-chloromethyl)-2,4,6-trimethylbenzene (1.0 mmol) and N-(2,4,6-trimethylphenyl)imidazoline (2.0 mmol) was heated in xylene (5 mL) at 120° C. for 48 hours and furnished the salt shown in Run F of Table 6 in 85% yield.

Example 7

The procedure used in all runs of this example are as follows: A Schlenk tube was charged with $Pd(CH_3CO_2)_2$ (5.6 mg, 0.025 mmol), one of the carbenes prepared in Example 6 (0.025 mmol), $CS_2CO_3$ (2.00 equivalents), and a magnetic stirring bar. After a 30 minute catalyst activation period, 1,4-dioxane (3 mL), 4-chlorotoluene (1.0 mmol), and phenylboronic acid (1.5 mmol) were added in turn to the Schlenk tube. The Schlenk tube was placed in a 80° C. oil bath and stirred for a number of hours. The mixture was then allowed to cool to room temperature. The bis(imidazoline-2-ylidene) used in each run are listed in Table 6. All of the yields reported in Table 6 are of the heterocoupling product, and are the average of two runs.

TABLE 6

| Run | Bis(imidazolinium) salt | Reaction time | Isolated yield |
|---|---|---|---|
| A | 4-MeOPh—N(+)N—CH$_2$—N(+)N—Ph-4-OMe •2Br$^\ominus$ | 24 hr. | trace[a] |
| B | 3,5-DiMePh—N(+)N—CH$_2$—N(+)N—Ph-3,5diMe •2Br$^\ominus$ | 24 hr. | <5%[a] |
| C | 2,4,6-TriMePh—N(+)N—CH$_2$—N(+)N—Ph-2,4,6-triMe •2Br$^\ominus$ | 6 hr. | 32%[a] |

TABLE 6-continued

| Run | Bis(imidazolinium) salt | Reaction time | Isolated yield |
|---|---|---|---|
| D | 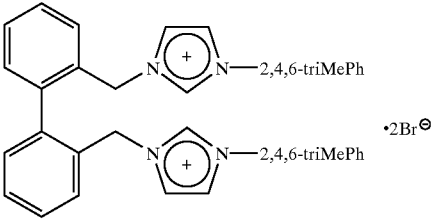 | 4 hr. | 65%[a] |
| E | 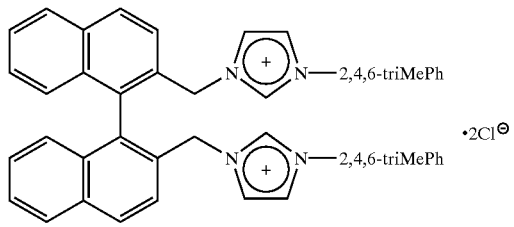 | 4 hr. | 87% |
| F | 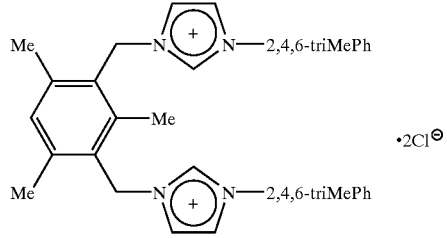 | 1.5 hr. | 99% |

[a] 4-Chlorotoluene was not completely consumed and precipitation of Pd black was observed.

Example 8

The procedure used in all runs of this Example was as follows: A Schlenk tube was charged with charged with $Pd(CH_3CO_2)_2$ (5.6 mg, 0.025 mmol), 1,3-bis(2,4,6-trimethylphenyl)imidazolinium chloride (10 mg, 0.025 mmol; Run a) or the bis(imidazolinium)dichloride shown in Run F of Table 6 (16 mg, 0.025 mmol; Runs b–h), $Cs_2CO_3$ (652 mg, 2.00 mmol), and a magnetic stirring bar. After a 30 minute catalyst activation period, 1,4-dioxane (3 mL), aryl chloride (1.0 mmol), and arylboronic acid (1.5 mmol) were added in turn to the Schlenk tube. The Schlenk tube was placed in a 80° C. oil bath and stirred for a number of hours. The mixture was then allowed to cool to room temperature. The aryl chlorides and arylboronic acids used in each run are listed in Table 7, along with the reaction times and isolated yields of the heterocoupling product.

TABLE 7

| Run | Aryl chloride | Arylboronic acid | Reaction time | Isolated yield |
|---|---|---|---|---|
| a | 4-Chlorotoluene | 2-Methylphenyl-boronic acid | 4 hr. | 60% |
| b | 4-Chlorotoluene | 2-Methylphenyl-boronic acid | 4 hr. | 99% |
| c | 4-Chlorotoluene | Phenylboronic acid | 1.5 hr. | 99% |
| d | 4-Chlorotoluene | 4-Methylphenyl-boronic acid | 4 hr. | 99% |
| e | 1,4-Dimethyl-2-chlorobenzene | Phenylboronic acid | 4 hr. | 84% |
| f | Methyl-4-chlorobenzoate | Phenylboronic acid | 2 hr. | 99% |
| g | 1-Me-3-ethylate-4-(4-Clphenyl)piperidine | Phenylboronic acid | 4 hr. | 96% |
| h | 1-Me-4-cyano-4-(4-Clphenyl)piperidine | Phenylboronic acid | 4 hr. | 91% |

It is to be understood that the reactants and components referred to by chemical name or formula anywhere in the specification or claims hereof, whether referred to in the singular or plural, are identified as they exist prior to coming into contact with another substance referred to by chemical name or chemical type (e.g., another reactant, a solvent, etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. Whatever transformations, if any, that occur in situ as a reaction is conducted is what the claim is intended to cover. Thus the fact that a substance, component or ingredient may have lost its original identity through a chemical reaction or transformation during the course of contacting, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof.

Each and every patent or other publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A process for conducting a reaction in which a coupling product is formed, which process comprises mixing, in a liquid medium, i) at least one strong base;
    ii) at least one aryl halide or aryl pseudohalide in which all substituents are other than boronic acid groups, wherein the aryl halide has, directly bonded to the aromatic ring(s), at least one halogen atom selected from the group consisting of a chlorine atom, a bromine atom, and an iodine atom;
    iii) at least one arylboronic acid in which all substituents are other than chlorine atoms, bromine atoms, iodine atoms, or pseudohalide groups;
    iv) at least one metal compound comprising at least one metal atom selected from nickel, palladium, and platinum, wherein the formal oxidation state of the metal is zero or two; and
    v) at least one N-heterocyclic carbene selected from the group consisting of an imidazoline-2-ylidene wherein the 1 and 3 positions are each, independently, substituted by a secondary or tertiary group which has at least three atoms, or a protonated salt thereof; an imidazolidine-2-ylidene wherein the 1 and 3 positions are each, independently, substituted by a secondary or tertiary group which has at least three atoms, or a protonated salt thereof; a bis(imidazoline-2-ylidene) wherein a bridging moiety is bound to one nitrogen atom of each ring, and wherein the remaining two nitrogen atoms are each, independently, substituted by a secondary or tertiary group which has at least three atoms, or a protonated salt thereof; and a bis(imidazolidine-2-ylidene) wherein a bridging moiety is bound to one nitrogen atom of each ring, and wherein the remaining two nitrogen atoms are each, independently, substituted by a secondary or tertiary group which has at least three atoms, or a protonated salt thereof; and mixtures of two or more of the foregoing.

2. A process according to claim 1 wherein said N-heterocyclic carbene is an imidazoline-2-ylidene of the formula

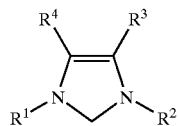

or a protonated salt thereof, wherein $R^1$ and $R^2$ are each, independently, alkyl or aryl groups having at least 3 carbon atoms, and $R^3$ and $R^4$ are each, independently, a hydrogen atom, a halogen atom, or a hydrocarbyl group.

3. A process according to claim 1 wherein said N-heterocyclic carbene is an imidazolidine-2-ylidene of the formula

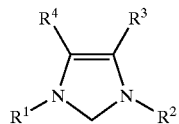

or a protonated salt thereof, wherein $R^1$ and $R^2$ are each, independently, alkyl or aryl groups having at least 3 carbon atoms, and $R^3$ and $R^4$ are each, independently, a hydrogen atom, a halogen atom, or a hydrocarbyl group.

4. A process according to claim 1 wherein said N-heterocyclic carbene is a bis(imidazoline-2-ylidene) of the formula

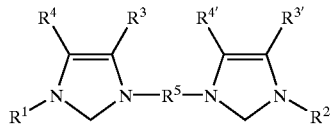

or a protonated salt thereof, wherein $R^1$ and $R^2$ are each, independently, alkyl or aryl groups having at least 3 carbon atoms, $R^3$ and $R^4$ are each, independently, a hydrogen atom, a halogen atom, or a hydrocarbyl group, $R^{3'}$ and $R^{4'}$ are as defined for $R^3$ and $R^4$, and $R^5$ is a bridging group that links the two imidazoline rings.

5. A process according to claim 1 wherein said N-heterocyclic carbene is a bis(imidazolidine-2-ylidene) of the formula

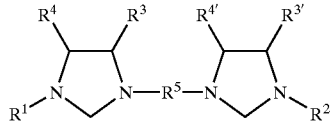

or a protonated salt thereof, wherein $R^1$ and $R^2$ are each, independently, alkyl or aryl groups having at least 3 carbon atoms, $R^3$ and $R^4$ are each, independently, a hydrogen atom, a halogen atom, or a hydrocarbyl group, $R^{3'}$ and $R^{4'}$ are as defined for $R^3$ and $R^4$, and $R^5$ is a bridging group that links the two imidazoline rings.

6. A process according to claim 1 wherein said liquid medium comprises at least one ether.

7. A process according to claim 6 wherein said ether is a cyclic ether.

8. A process according to claim 7 wherein said ether is 1,4-dioxane.

9. A process according to claim 1 wherein said aryl halide or aryl pseudohalide is an aryl chloride.

10. A process according to claim 9 wherein said aryl chloride is selected from the group consisting of 4-chlorotoluene, 1-methoxy-4-chlorobenzene, and 1,4-dimethyl-2-chlorobenzene.

11. A process according to claim 1 wherein said aryl halide or aryl pseudohalide is an aryl toluenesulfonate.

12. A process according to claim 11 wherein said aryl toluenesulfonate is 4-methylphenyltoluenesulfonate.

13. A process according to claim 1 wherein said aryl halide or aryl pseudohalide is an aryl trifluoromethanesulfonate.

14. A process according to claim 13 wherein said aryl trifluoromethanesulfonate is 1-methoxy-4-(trifluoromethanesulfonate)benzene.

15. A process according to claim 1 wherein said aryl halide or aryl pseudohalide is a phenyl halide or phenyl pseudohalide.

16. A process according to claim 15 wherein said phenyl halide or phenyl pseudohalide is chlorobenzene.

17. A process according to claim 1 wherein said aryl halide or aryl pseudohalide is a naphthyl halide or naphthyl pseudohalide.

18. A process according to claim 17 wherein said naphthyl halide or naphthyl pseudohalide is 2-bromonaphthalene.

19. A process according to claim 1 wherein said arylboronic acid is a phenylboronic acid.

20. A process according to claim 19 wherein said phenylboronic acid is selected from the group consisting of 2-methylphenylboronic acid, 4-methylphenylboronic acid, 4-methoxyphenylboronic acid, and phenylboronic acid.

21. A process according to claim 1 wherein said arylboronic acid is a naphthylboronic acid.

22. A process according to claim 21 wherein said naphthylboronic acid is 6-methoxy-2-naphthylboronic acid.

23. A process according to claim 1 wherein said metal compound comprises a palladium compound.

24. A process according to claim 23 wherein said palladium compound is selected from the group consisting of palladium acetate, palladium chloride, and dipalladium tris (dibenzylideneacetone).

25. A process according to claim 1 wherein said metal compound comprises a nickel compound.

26. A process according to claim 25 wherein said nickel compound is bis(1,5-cyclooctadiene)nickel.

27. A process according to claim 26 wherein said strong base is cesium carbonate.

28. A process according to claim 1 wherein said strong base is an alkali metal salt.

29. A process according to claim 28 wherein said alkali metal salt is either a potassium salt or a cesium salt.

30. A process according to claim 29 wherein said salt is selected from the group consisting of potassium carbonate, potassium tert-butoxide, and cesium carbonate.

31. A process according to claim 1 wherein said strong base is cesium carbonate, wherein the metal compound is selected from the group consisting of palladium acetate, palladium chloride, and dipalladium tris (dibenzylideneacetone), and wherein the aryl halide or aryl pseudohalide is an aryl chloride.

32. A process according to claim 1 wherein said strong base is either potassium carbonate or cesium carbonate, wherein the metal compound is selected from the group consisting of palladium acetate, palladium chloride, and dipalladium tris(dibenzylideneacetone), and wherein the aryl halide or aryl pseudohalide is either an aryl trifluoromethanesulfonate or an aryl toluenesulfonate.

33. A process according to claim 1 wherein said N-heterocyclic carbene is an imidazoline-2-ylidene or a protonated salt thereof.

34. A process according to claim 2 wherein $R^1$ and $R^2$ of said N-heterocyclic carbene are the same, and each is either a 2,4,6-trimethylphenyl group or a 2,6-diisopropylphenyl group.

35. A process according to claim 3 wherein $R^1$ and $R^2$ of said N-heterocyclic carbene are the same, and each is either a 2,4,6-trimethylphenyl group or a 2,6-diisopropylphenyl group.

36. A process according to claim 4 wherein $R^1$ and $R^1$ of said N-heterocyclic carbene are the same, and each is either a 2,4,6-trimethylphenyl group or a 2,6-diisopropylphenyl group.

37. A process according to claim 5 wherein $R^1$ and $R^2$ of said N-heterocyclic carbene are the same, and each is either a 2,4,6-trimethylphenyl group or a 2,6-diisopropylphenyl group.

38. A process according to claim 34 wherein said N-heterocyclic carbene is a protonated salt of an imidazoline-2-ylidene.

39. A process according to claim 2 wherein $R^3$ and $R^4$ of said N-heterocyclic carbene are the same, and each is a hydrogen atom.

40. A process according to claim 3 wherein $R^3$ and $R^4$ of said N-heterocyclic carbene are the same, and each is a hydrogen atom.

41. A process according to claim 4 wherein $R^3$ and $R^4$ of said N-heterocyclic carbene are the same, and each is a hydrogen atom.

42. A process according to claim 5 wherein $R^3$ and $R^4$ of said N-heterocyclic carbene are the same, and each is a hydrogen atom.

43. A process according to claim 34 wherein $R^3$ and $R^4$ of said N-heterocyclic carbene are the same, and each is a hydrogen atom.

44. A process according to claim 34 wherein said strong base is a cesium salt and wherein said metal compound is a palladium compound.

45. A process according to claim 44 wherein said cesium salt is cesium carbonate and wherein said palladium compound is selected from the group consisting of palladium acetate, palladium chloride, and dipalladium tris (dibenzylideneacetone).

46. A process according to claim 34 wherein the molar ratio of metal atoms of the metal compound to aryl halide or aryl pseudohalide molecules is in the range of from about 0.01:1 to about 0.05:1.

47. A process according to claim 4 wherein said N-heterocyclic carbene is a protonated salt of a bis (imidazoline-2-ylidene).

48. A process according to claim 47 wherein $R^1$ and $R^2$ of said protonated salt are the same, and each is a 2,4,6-trimethylphenyl group or a 2,6-diisopropylphenyl group.

49. A process according to claim 47 wherein $R^{3'}$ and $R^{4'}$ of said protonated salt are the same, and each is a hydrogen atom.

50. A process according to claim 4 wherein $R^{3'}$ and $R^{4'}$ of said N-heterocyclic carbene are the same, and each is a hydrogen atom.

51. A process according to claim 5 wherein $R^{3'}$ and $R^{4'}$ of said N-heterocyclic carbene are hydrogen atoms.

52. A process according to claim 47 wherein $R^3$ and $R^4$ of said protonated salt are the same, and each is a hydrogen atom.

53. A process according to claim 48 wherein said strong base is a cesium salt and wherein said metal compound is a palladium compound.

54. A process according to claim 53 wherein said cesium salt is cesium carbonate and wherein said palladium compound is palladium acetate.

55. A process according to claim 48 wherein the molar ratio of metal atoms of the metal compound to aryl halide or aryl pseudohalide molecules is in the range of from about 0.01:1 to about 0.05:1.

56. A process according to claim 48 wherein said protonated salt of the bis(imidazoline-2-ylidene) is

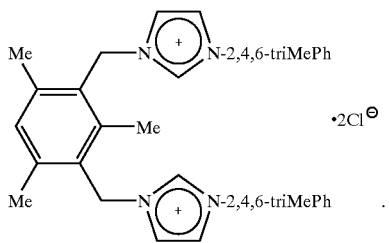

57. A process according to claim 4 wherein the bridge formed by $R^5$ has at least four atoms.

58. A process according to claim 57 wherein the bridge formed by $R^1$ has four to eight atoms.

59. A process according to claim 5 wherein the bridge formed by $R^1$ has four to eight atoms.

60. A process according to claim 4 wherein $R^1$ is a substituted benzo moiety.

61. A process according to claim 5 wherein $R^5$ is a substituted benzo moiety.

62. A process according to claim 1 wherein the molar ratio of aryl halide or aryl pseudohalide to arylboronic acid is in the range of from about 1:1 to about 1:3.

63. A process according to claim 1 wherein the molar ratio of aryl halide or aryl pseudohalide to strong base is in the range of from about 1:1 to about 1:5.

64. A process according to claim 1 wherein the molar ratio of metal atoms of the metal compound to aryl halide or aryl pseudohalide molecules is in the range of from about 0.01:1 to about 0.05:1.

65. A process according to claim 1 wherein the molar ratio of metal atoms of the metal compound to N-heterocyclic carbene is in the range of from about 1:0.5 to about 1:5.

66. A process according to claim 1 wherein the temperature is in the range of from about 20° C. to about 150° C.

67. A process according to claim 1 wherein the temperature is in the range of from about 20° C. to about 110° C.

68. A process according to claim 1 wherein said aryl halide or aryl pseudohalide is selected from the group consisting of an aryl chloride, an aryl tosylate, and an aryl triflate, and wherein the temperature is in the range of from about 40° C. to about 150° C.

69. A process according to claim 1 wherein said aryl halide or aryl pseudohalide is either an aryl bromide or an aryl iodide, and wherein the temperature is in the range of from about 20° C. to about 70° C.

* * * * *

UNITED STATES PATENT AND TRADEMARK OFFICE
CERTIFICATE OF CORRECTION

PATENT NO. : 6,403,801 B1
DATED : June 11, 2002
INVENTOR(S) : Steven P. Nolan et al.

It is certified that error appears in the above-identified patent and that said Letters Patent is hereby corrected as shown below:

Title page,
Item [54], title, replace "USE OF A CATALYST SYSTEM COMPRISING NICKEL, PALLADIUM, OR PLATINUM AND IMIDAZOLINE-2-YLIDENE OF IMIDAZOLIDINE-2-YLIDENE IN SUZUKI COUPLING REACTIONS" with -- USE OF A CATALYST SYSTEM COMPRISING NICKEL, PALLADIUM, OR PLATINUM AND IMIDAZOLINE-2-YLIDENE OR IMIDAZOLIDINE-2-YLIDENE IN SUZUKI COUPLING REACTIONS --.

Column 5,
Line 18, replace the following formula
"
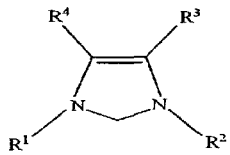
"

with --
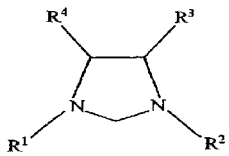
--.

Column 16,
Line 19, replace the following formula
"
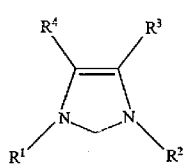
"

with --
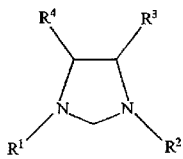
--.

UNITED STATES PATENT AND TRADEMARK OFFICE
CERTIFICATE OF CORRECTION

PATENT NO.    : 6,403,801 B1
DATED         : June 11, 2002
INVENTOR(S)   : Steven P. Nolan et al.

It is certified that error appears in the above-identified patent and that said Letters Patent is hereby corrected as shown below:

Column 18,
Line 17, replace "$R^1$" with -- $R^2$ --.

Column 19,
Line 29, replace "$R^1$" with -- $R^5$ --.
Line 31, replace "$R^1$" with -- $R^5$ --.
Line 32, replace "$R^1$" with -- $R^5$ --.

Signed and Sealed this

Seventh Day of January, 2003

JAMES E. ROGAN
*Director of the United States Patent and Trademark Office*